United States Patent [19]
Roche et al.

[11] Patent Number: 5,891,651
[45] Date of Patent: Apr. 6, 1999

[54] METHODS OF RECOVERING COLORECTAL EPITHELIAL CELLS OR FRAGMENTS THEREOF FROM STOOL

[75] Inventors: Patrick C. Roche; George G. Klee; Paul J. Limburg; David A. Ahlquist, all of Rochester, Minn.

[73] Assignee: Mayo Foundation for Medical Education and Research, Rochester, Minn.

[21] Appl. No.: 625,015

[22] Filed: Mar. 29, 1996

[51] Int. Cl.$^6$ .......................... G01N 33/53; G01N 33/537; G01N 33/541; G01N 33/574

[52] U.S. Cl. .......................... 435/7.21; 435/7.23; 435/7.94

[58] Field of Search .................................. 435/7.23, 7.21, 435/7.94

[56] References Cited

PUBLICATIONS

Arlen and Tsang, "The Nature of the Monoclonal Antibodies Derived from Immunogenic Membrane Antigen of Human Colon Carcinoma Origin," *Journal of Tumor Marker*, vol. 5, No. 4, 1990, pp. 313–319.
Arlen, Tsang, et al., "Monoclonal Antibodies to Immunoreactive Tumor Associated Antigen (TAA) from Human Colon Carcinoma," *Antibody Immunoconjugates and Radiopharmaceuticals*, vol. 4, No. 4, 1991, pp. 895–905.
Iyengar, Albaugh, Loani & Nair, "Human Stools as a Source of Viable Colonic Epithelial Cells," *FASEB*, 5: 2856–2859, 1991.
Watanabe, Mouri, et al., "The Colon Mucus Test in Comparison With the Fecal Occult Blood Test in the Detection of Gastrointestinal Disease," *Digestive Endoscopy*, 1992, 4:139–146.
Xu, Sakamoto, et al., "Detection of the Tumor Mark D–Galactose–$\beta$–(1→3)–N–Acetyl–D–galactosamine in Colonic Cancer and Precancer," *Arch Pathol Lab Med*, vol. 116, Nov. 1992, pp. 1234–1238.
Albaugh, Iyengar, et al., "Isolation of Exfoliated Colonic Epithelial Cells, A Novel Non–Invasive Approach to the Study of Cellular Markers," *Int. J. Cancer*:52, 347–350 (1992).
Arlen and Tsang, "Monoclonal Antibodies and Their Role In Modulation of the Immune Response," *Journal of Surgical Oncology* 54:103–108 (1993).
Shamsuddin and Sakamoto, "Carbohydrate Tumer Marker: Basis for a Simple Test for Colorectal Cancer," *Diet and Cancer: Markers, Prevention, and Treatment*, Ed. Jacobs, Plenum Press, NY, pp. 85–98, 1993.
Sakamoto, Muratani, et al., "Evaluation of a New Test for Colorectal Neoplasms: A Prospective Study of Asymptomatic Population," *Cancer Biotherapy*, 8:1:49–55 1993.
Abstract—Fecal marker Variability in Colorectal Cancer: Calprotectin Versus Hemoglobin, Apr. 1995, Gastroenterology, vol. 108, No. 4, p. A474.
Abstract—Candidate Stool Markers for Colorectal Cancer Screening: An Immunohistochemical Analysis, Apr. 1995, Gastroenterology, vol. 108, No. 4, p. A473.
Murphy, S.J. et al. 1992 J. Cell Science 102: 789–798.
Wang, S.Y. et al. 1993, Anticancer Res. 13: 2281–2286.
Heyderman, E. et al. 1984, J. Clin. Pathol. 37: 1363–1369.
Thomas; M. G. et al. 1994 Gut, 35: 1742–1746.
Kotera, Y. et al. 1994. Cancer Res. 54: 2856–2860.
Dion, A.S. et al. 1991. Hybridoma, 5: 595–610.
Han, K.A. 1992—Cancer Res, 52: 749–753.
Spaulding, M. 1994, Packaging 39:29–31.
Islam, D. et al. 1993. Eur. J. Clin. Microb. Infect. Dis. 12(1):25–32.

*Primary Examiner*—Lila Feisee
*Assistant Examiner*—Nancy A. Johnson
*Attorney, Agent, or Firm*—Fish & Richardson, P.C., P.A.

[57] ABSTRACT

A method of recovering colorectal epithelial cells or fragments thereof from a stool sample is provided. The method involves contacting a stool sample with a specific binding reagent having specificity for colorectal epithelial cells or membrane fragments thereof to form a complex containing the specific binding reagent and the colorectal epithelial cells or fragments thereof, and separating the complex from the sample. A method of detecting dysplastic colorectal epithelial cells or fragments thereof, wherein a specific binding reagent employed in the method has specificity for dysplastic colorectal epithelial cells or membrane fragments thereof, is also provided. An article of manufacture containing reagents for performing the method is further provided.

15 Claims, 2 Drawing Sheets

METHODS OF RECOVERING COLORECTAL EPITHELIAL CELLS OR FRAGMENTS THEREOF FROM STOOL

FIELD OF THE INVENTION

The invention relates to methods of recovering colorectal epithelial cells or fragments thereof from stool. Specifically, the invention relates to methods of using specific binding reagents to recover colorectal epithelial cells or fragments thereof from stool samples, and further to the use of such methods in the early detection of colorectal neoplasia by the presence in stool of dysplastic epithelial cells or fragments thereof.

BACKGROUND OF THE INVENTION

Colorectal cancer mortality ranks second among all causes of malignant death in industrialized nations. Recognition and curative treatment of precursor (premalignant) adenomas and localized cancers is possible with early detection.

Currently fecal occult blood testing is a widely utilized screening tool for the early detection of colorectal neoplasia, but suffers from several disadvantages. Fecal blood testing measures an ambiguous marker for colorectal neoplasia—hemoglobin—and tests for hemoglobin in stool samples have proved to be neither specific nor sufficiently sensitive. Recent reports indicate that fecal blood testing fails to detect over 70 percent of pre-malignant polyps. Colorectal neoplasms bleed intermittently, and thus fecal occult blood is not a reliable marker for colorectal neoplasia. Moreover, there are many causes of gastrointestinal bleeding unrelated to colorectal neoplasia, resulting in a very high level of false positives using the fecal occult blood screening method. False positives result in unnecessary and costly follow-up procedures such as colonoscopy.

In terms of simplicity, however, stool testing approaches the ideal for colorectal cancer screening; it is non-invasive, has a low unit cost, generates reasonably high compliance, and reflects the entire colorectal surface. A specific and sensitive stool screening test for colorectal neoplasia would thus be extremely valuable.

Exfoliated dysplastic epithelial cells represent a possible stool marker for colon cancer. Such cells obtained from lavage effluents have been shown to be reliable markers of colorectal cancer, but specimen collection required the invasive technique of colorectal purgation, limiting the clinical utility of this approach. Recently, a density gradient centrifugation technique was developed to collect sloughed colonocytes from routine stool samples. This technique, however, is time-consuming and technically complex, and therefore does not allow for an efficient and selective recovery of colorectal epithelial cells, is not amenable to large volume processing, and thus is not useful as a stool screening technique of the type currently needed.

SUMMARY OF THE INVENTION

The present invention provides an efficient and selective method of recovering colorectal epithelial cells or fragments thereof from stool, and overcomes the disadvantages associated with the density gradient centrifugation technique currently available in the art. The present invention further provides a screening technique for colorectal neoplasia that is markedly superior to the fecal occult blood detection technique currently utilized. In one aspect, the present invention relates to a method of recovering colorectal epithelial cells or fragments thereof from a stool sample. The method involves the steps of (a) contacting a stool sample containing colorectal epithelial cells or fragments thereof with a specific binding reagent having specificity for colorectal epithelial cells or fragments thereof to form complexes comprising said specific binding reagent and said colorectal epithelial cells or fragments thereof, and (b) separating the complexes from the sample.

In preferred embodiments of the present invention, the specific binding reagent is selected from the group consisting of an antibody or antibody fragment having specificity for carcinoembryonic antigen, an antibody or antibody fragment having specificity for epidermal growth factor receptor, an antibody or antibody fragment having specificity for colon specific antigen, an antibody or antibody fragment having specificity for MUC-1 antigen, the antibody MA5 or an active fragment thereof, the antibody PCA 33.28 or an active fragment thereof, an antibody or antibody fragment having specificity for P53 antigen or mutant forms of P53 antigen, and mixtures thereof.

In other preferred embodiments of the present invention, the method further comprises the step of analyzing the colorectal epithelial cells or fragments thereof. The analyzing of the colorectal epithelial cells or fragments thereof may include staining the colorectal epithelial cells or fragments thereof and microscopically examining the cells or fragments.

In other preferred embodiments, analyzing the colorectal epithelial cells or fragments thereof comprises determining the presence or absence of dysplastic colorectal epithelial cells or fragments thereof. Determining the presence or absence of dysplastic colorectal epithelial cells or fragments thereof may include immunostaining the colorectal epithelial cells or fragments thereof. The immunostaining may include contacting the colorectal epithelial cells or fragments thereof with a specific binding reagent having specificity for dysplastic colorectal epithelial cells or fragments thereof.

In other embodiments of the present invention, the specific binding reagent may have specificity for dysplastic colorectal epithelial cells or fragments thereof. Such specific binding reagents may be selected from the group consisting of an antibody or active antibody fragment having specificity for MUC-1 antigen, the antibody MA5 or an active fragment thereof, the antibody PCA 33.28 PCA or an active fragment thereof, an antibody or active antibody fragment having specificity for P53 or any mutuant form of P53 antigen, and mixtures thereof. In this embodiment of the invention, the method may further comprise the step of determining the presence or absence of dysplastic colorectal epithelial cells or fragments thereof in the stool sample. Determining the presence or absence of dysplastic colorectal epithelial cells or fragments thereof may involve staining and microscopically examining the dysplastic colorectal epithelial cells or fragments thereof complexed with said specific binding reagent having specificity for dysplastic colorectal epithelial cells or fragments thereof.

In preferred embodiments of the present invention, the contacting step comprises contacting the stool sample with a magnetic bead containing the specific binding reagent. In this embodiment, the separating step preferably comprises magnetically separating said complex from said sample.

In another aspect, the present invention relates to a method of detecting dysplastic colorectal epithelial cells and fragments thereof in a stool sample. The method involves (a) contacting a stool sample with a first specific binding reagent having specificity for colorectal epithelial cells or fragments thereof to form first complexes comprising said first specific binding reagent and said colorectal epithelial cells and fragments thereof, (b) separating said first complexes from said sample, (c) contacting the first complexes or colorectal epithelial cells or fragments thereof recovered from said first complexes with a second specific binding reagent having specificity for dysplastic colorectal epithelial cells or fragments thereof to form second complexes containing the second specific binding reagent and the dysplastic colorectal epithelial cells or fragments thereof, (d) separating the second complexes from the sample solution, and (e) determining the presence or absence of dysplastic colorectal epithelial cells in the stool sample. Determining the presence or absence of dysplastic colorectal epithelial cells or fragments thereof preferably involves contacting the second complexes with a third specific binding reagent having specificity for the second specific binding reagent, separating bound third specific binding reagent from free third specific binding reagent, and determining the presence of bound third specific binding reagent.

In another aspect the present invention relates to an article of manufacture containing packaging material and reagents contained within the packaging material, wherein the reagents are effective for recovering colorectal epithelial cells or fragments thereof from stool, and wherein the packaging material contains a label indicating that the reagents can be used for recovering colorectal epithelial cells or fragments thereof from stool, and wherein the reagents contain a specific binding reagent having specificity for colorectal epithelial cells or fragments thereof.

As used herein, "colorectal epithelial cell or fragment thereof" means any normal or dysplastic (abnormal) cell or fragment derived from normal or diseased colorectal epithelium.

As used herein, "fragment" means any degradation product (resulting from mechanical, chemical, or biochemical degradation) of a colorectal epithelial cell containing a binding partner for a specific binding reagent having specificity for colorectal epithelial cells, such as a membrane fragment.

As used herein, "specific binding reagent" means monoclonal or polyclonal antibodies, a protein or peptide, or other agent that will immunologically bind, or specifically adhere, to a colorectal epithelial cell or fragment thereof.

The invention provides an efficient and selective method of recovering colorectal epithelial cells or fragments thereof from stool, by exploiting a specific binding reaction between a specific binding reagent and colorectal epithelial cells or fragments thereof to segregate, or isolate, colorectal epithelial cells or fragments thereof from stool. The invention thus provides a highly desirable alternative to the currently available density gradient centrifugation technique of recovering colorectal epithelial cells, which is time-consuming, technically complex, and not a feasible method for large volume processing required in a screening technique for the asymptomatic general population. The present invention has additional advantages over the density gradient centrifugation technique described in the art. The method of this invention allows for the recovery of cell fragments containing antigenic markers (or other specific binding partners) which would not be recovered in the density gradient technique (but which have analytical or diagnostic significance) because such fragments are not isodense with whole cells. In addition, the use of specific binding reagents eliminates contaminating isodense debris, which is present with cells, in material recovered using the density gradient procedure. The invention thus provides a source of colorectal epithelial cells or fragments thereof for any type of clinical or laboratory testing, including the use of such cells or fragments in the early detection of colorectal neoplasia.

The invention also provides methods of detecting dysplastic colorectal epithelial cells or fragments thereof, which cells or fragments are suggestive of colorectal neoplasia. These methods are amenable to large volume processing and could thus serve as a screen for the large asymptomatic population. This screening technique is markedly superior to fecal blood testing.

The method provides several important advantages over fecal blood testing, currently the most widely used screening technique. The method of this invention detects cellular markers which are more specific as markers of colorectal neoplasia than fecal blood, and thus the method is more accurate, greatly reducing the incidence of false positives and the unnecessary and costly colonoscopic evaluation following a false positive result. The reduction of false positives achieved by the present invention is extremely important to a screening intervention aimed at a general population.

DESCRIPTION OF THE PREFERRED EMBODIMENTS

Figure 1:
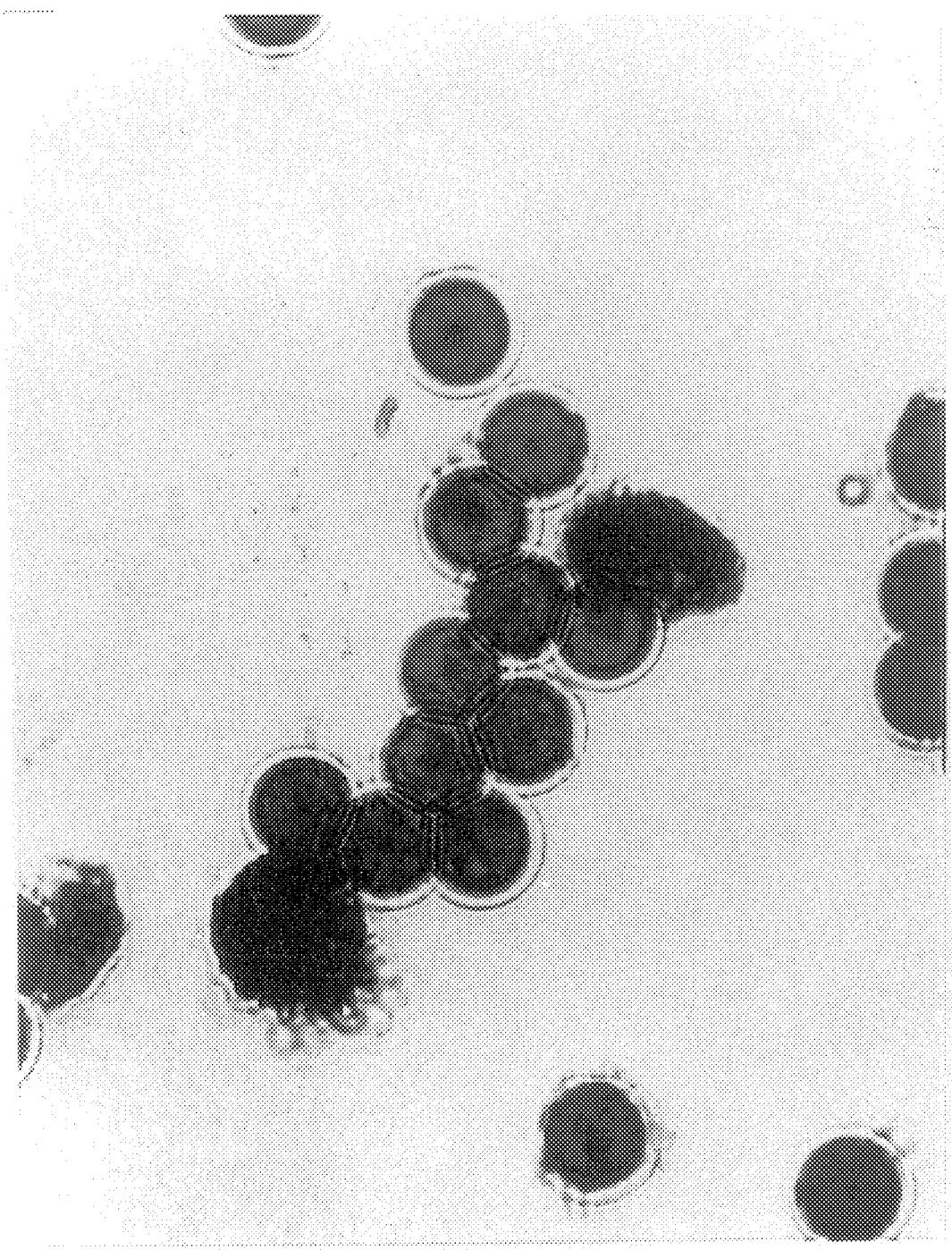
FIG. 1 is a photomicrograph of immunocaptured colorectal epithelial cells.

This invention relates to a method of recovering exfoliated colorectal epithelial cells or fragments thereof from a stool sample.

Exfoliated colorectal epithelial cells represent a potentially significant source of material for obtaining data regarding the status of the colorectal epithelium and for testing and screening for colorectal neoplasia. As many as one-third of cells from the epithelial surface are shed into the lumen each day. Because of extensive surface involutions, it has been estimated that an adenoma of only 1.0 cm has a surface area equal to about 1 percent of the colorectum; thus cells from clinically important neoplasms may represent a quantitatively substantial contribution to the exfoliated population. It is also likely that cellular fragments, including membrane fragments, resulting from mechanical, chemical, or biochemical degradation processes, appear in stool.

The only means heretofore known of obtaining colorectal epithelial cells from stool involved density gradient centrifugation, a time-consuming and technically complex technique. Nair et al., *FASEB J.*, 5:2856–2859 (1991).

Accordingly, the present invention provides a method of capturing colorectal epithelial cells or fragments thereof from a stool sample by exploiting a specific binding reaction between a specific binding reagent and colorectal epithelial cells or fragments thereof in the sample.

In one embodiment, the invention provides a method of recovering colorectal epithelial cells or fragments thereof from a stool sample.

Stool samples suitable for use in the present invention are readily obtained. Such samples may be obtained by the donor individually and presented to a laboratory for testing, or are easily obtained in the clinical setting. Typically, a stool sample of several grams is placed in a transport medium. A suitable transport medium is typically a buffered solution containing an anti-bacterial agent, such as 0.5% thimerasol, and a mucolytic agent, such as N-acetyl cysteine. The sample is preferably delivered to a laboratory within 24 hours, preferably on ice. In the laboratory, a dispersing medium typically is added, and the sample is further dispersed in a laboratory blender such as a stomacher. The sample may then be tested. The sample may also be centrifuged, the supernatant discarded, and the pellet resuspended, resulting in a sample ready for testing.

In accordance with the invention, the stool sample is contacted with a specific binding reagent having specificity for colorectal epithelial cells or membrane fragments thereof. Many such specific binding reagents are known. The invention contemplates that any specific binding reagent having specificity for colorectal epithelial cells or fragments thereof is useful in the practice of the invention. Carcinoembryonic antigen (CEA) is commonly expressed in non-neoplastic and neoplastic epithelium, and antibodies or active antibody fragments specific to CEA are useful for capturing exfoliated colorectal epithelial cells or fragments thereof in the present invention. Other non-limiting examples of specific binding agents useful in the capture of colorectal epithelial cells include antibodies or active antibody fragments specific to the epidermal growth factor receptor (EGFR), and antibodies or active antibody fragments specific to colon specific antigen (CSA).

Certain specific binding reagents are useful in the capture or detection of dysplastic colorectal epithelial cells or fragments thereof because they have specificity for markers (binding partners) that are expressed or overexpressed on dysplastic cells exfoliated from colorectal neoplasms. Any specific finding reagent having specificity for dysplastic colorectal epithelial cells or fragments thereof is useful in the practice of the present invention. Such specific binding reagents may include: antibodies or active antibody fragments having specificity for MUC-1 antigen or other mucins that are expressed or overexpressed dysplastic colorectal epithelial cells, antibodies or active antibody fragments having specificity for P53 protein or mutants thereof, the antibody MA5 or active fragments thereof, and the antibody PCA 33.28 or active fragments thereof (PCA 33.28 described in Arlen et al., *J. Tumor Marker Oncology*, 5:4:p. 313–319 (1990).

The contacting step of the invention may be effected in a variety of formats known to those of skill in the art. For example, the contacting step may involve incubating the stool sample with a solution containing the specific binding reagent under conditions allowing the specific binding reagent to form a complex with colorectal epithelial cells or membrane fragments thereof from the stool sample. Such conditions, such as temperature, pH, and incubation time are well known to those of skill in this art. Preferably, the method of the present invention is performed at a pH of 7.2. To maximize recovery, a mixture of specific binding reagents may be used. This may be achieved by using beads coated with a mixed population of specific binding reagents, or by using a mixture of beads, each coated with a particular specific binding reagent.

The contacting step may also involve incubating the stool sample with a solid phase containing the specific binding reagent under conditions allowing the specific binding reagent to form a complex containing the specific binding reagent and colorectal epithelial cells or fragments thereof from the stool sample. Such solid phase techniques are known in the art. Nonlimiting examples of such techniques include exposing the stool sample to a well, the surface of which is coated with the specific binding reagent, or incubating the stool sample with a suspension of beads coated with the specific binding reagent. In one preferred embodiment of the present invention, illustrated in the Examples below, the contacting step involves incubating the stool sample with magnetic beads coated with a specific binding reagent under conditions allowing binding of the specific binding reagent and colorectal epithelial cells or fragments thereof.

In one embodiment of the present invention, the specific binding reagent is one of the above-described specific binding reagents having specificity for dysplastic colorectal epithelial cells or fragments thereof. In this embodiment, the invention provides a method of specifically capturing dysplastic colorectal epithelial cells or fragments thereof. To maximize recovery, a mixture of specific binding reagents may be used.

The method of the invention further involves the step of separating the complexes (containing specific binding reagent and colorectal epithelial cells or fragments thereof) formed in the contacting step from the sample solution. The mode of separation will depend on the format employed in the contacting step. For example, in embodiments of the invention wherein the contacting step involves incubating the stool sample with a solubilized specific binding reagent, the separating step may involve capturing the complex containing the specific binding reagent and colorectal epithelial cells or fragments thereof with a second specific binding reagent, such as an antibody, having specificity for either the specific binding reagent in the complex or the colorectal epithelial cells or membrane fragments thereof in the complex. The second specific binding reagent may be attached to a solid phase such as a well or plate, or may be captured by a solid phase following binding to the complex. Alternatively, the complex may be contacted with, or coated onto, a solid phase such as a bead or other surface such as the surface of a well. The bead may then be separated from the sample solution, or the surface washed of the sample solution, using conventional methods known in the art.

As described above, in embodiments of the invention wherein the contacting step involves incubating the stool sample with a solid phase containing a specific binding reagent having specificity for colorectal epithelial cells or membrane fragments thereof, the solid phase may consist of the surface of a well or a bead. Where the solid phase is the surface of a well, the separating step may involve simply washing the sample solution from the well to thereby separate the complex formed on the solid phase in the contacting step from the sample solution. In embodiments of the invention wherein the solid phase is a bead containing a specific binding reagent, the separating step may involve centrifuging the sample to separate the beads containing the complex formed in the contacting step from the sample solution, removing the supernatant and resuspending the separated beads. In a preferred embodiment of the present invention, illustrated in the Examples below, a magnetic bead containing a specific binding reagent is used in the contacting step, and thus the separating step may involve exposing the sample to a magnet or incubating the sample in a magnetic chamber, discarding the supernatant, and resuspending the magnetic beads containing the complexed colorectal epithelial cells or fragments thereof and thereby separating the complex from the sample solution.

It should be recognized to those of skill in the art that any format may be used to separate the complex containing the colorectal epithelial cells or fragments thereof from the stool sample. The invention relates to the exploitation of a specific binding reaction to capture colorectal epithelial cells or fragments thereof from stool to form complexes containing the specific binding reagent and the cells or fragments thereof, and the separation of the complexes from the sample by any means described herein or known in the art. The invention is not limited by the formats used to effect the contacting or separating steps.

In accordance with the invention, the separating of the complexes formed in the contacting step effects a separation of colorectal epithelial cells or fragments thereof from the stool sample. The colorectal epithelial cells or fragments thereof in the separates complexes are thus available for analysis.

Accordingly, in preferred embodiments, the method of the invention further comprises analyzing the colorectal epithelial cells or fragments thereof.

The analysis of the colorectal epithelial cells or fragments thereof may involve any testing of the captured material, including detecting the presence of the cells or fragments, detecting the presence of dysplastic colorectal epithelial cells or fragments thereof that are suggestive of colorectal neoplasia, quantitating the recovery of the captured material. The analysis may also include assaying the cells or extracts thereof for a genetic alteration such as a mutation, or monitoring levels of a therapeutic substance in captured colorectal epithelial cells to determine appropriate dosage levels in patients suffering from, for example, inflammatory bowel disease or other gastrointestinal disorders.

In one embodiment of the invention, illustrated in the Examples below, the captured material, complexed with a specific binding reagent on a bead, is applied to a slide, stained with a staining material appropriate for viewing epithelial cells or membrane fragments thereofsuch as hematoxylin and eosin, and the stained material is viewed microscopically.

Other methods of analysis of the colorectal epithelial cells or fragments thereof include immunostaining the cells or fragments. This analysis may be achieved, for example, by exposing the separated complex to a second specific binding reagent such as one of those described herein, having specificity for the colorectal epithelial cells or fragments thereof. The complex may then be exposed to a third specific binding reagent, such as an antibody, which may contain part of a signal detection system. One nonlimiting example of such a signal detection system involves a biotinylated antibody to which streptavidin (which has high affinity for biotin) coupled to horseradish peroxidase may be added. Substrate for the enzyme may then be added and the enzymatic reaction produces a visible stain and the colorectal epithelial cells or fragments thereof are detected.

There are numerous methodologies for immunostaining or otherwise visualizing the captured colorectal epithelial cells or fragments thereof known in the art, and the present invention is not limited by any particular format or method of detecting the captured material.

If the second specific binding reagent in the above-described analysis has specificity for dysplastic colorectal epithelial cells or fragments thereof, this analysis provides a method for detecting dysplastic colorectal epithelial cells or fragments thereof.

Accordingly, the invention features a method of detecting dysplastic colorectal epithelial cells or fragments thereof in a stool sample. The method includes the steps of (a) contacting a stool sample with a first specific binding reagent having specificity for colorectal epithelial cells or fragments thereof to form first complexes comprising the first specific binding reagent and the colorectal epithelial cells or fragments thereof, (b) separating the first complexes from the sample, (c) contacting the first complexes, or colorectal epithelial cells or fragments thereof recovered from the first complexes, with a second specific binding reagent having specificity for dysplastic colorectal epithelial cells or fragments thereof to form second complexes comprising the second specific binding reagent and the dysplastic colorectal epithelial cells or fragments thereof, (d) separating said second complexes, and (e) determining the presence or absence of dysplastic colorectal epithelial cells in the stool sample.

A third specific binding reagent may be used in a detection procedure, such as immunostaining, as described above.

In accordance with the invention, the materials and conditions employed in this aspect of the invention may be those described above with reference to other preferred embodiments.

The invention may be illustrated by way of the following examples.

EXAMPLE 1

Preparation of Stool Samples

Donors were given collection kits containing a pre-weighed vial with 25 ml of transport medium and instructions to place approximately 2 grams (gm) of stool in the vial, shake gently to disperse the sample, and return the specimen to the laboratory on ice within 24 hours. Transport medium comprises a dispersing medium to which thimerosal (approximately 0.5 gm/L) is added as an anti-bacterial agent. Dispersing medium (pH 7.2) contains 0.5 gm of sodium bicarbonate, 5 gm of BSA (heat shocked and fatty acid free), 500 mL of Puck's saline G, and 0.25 g N-acetylcysteine (Sigma A-9165). Puck's saline G (Puck et al., *J. Exp. Med.* 108:945 (1958)) contains, in a 10X solution, in gm/L: 0.16 calcium chloride, 4.0 potassium chloride, 1.5 monobasic potassium phosphate, 1.54 magnesium sulfate, 80.0 sodium chloride, 1.54 dibasic sodium phosphate, 11.0 glucose, 0.05 phenol red. The 10X solution is prepared in deionized water and filter sterilized. To prepare the dispersing medium, the 10X solution is diluted with deionized water to 1X, and the sodium bicarbonate, N-acetyl cysteine, and bovine serum albumin are then added. Thimerosal is added to prepare the transport medium. pH for all solutions should be 7.2, and osmolality 290–310 Mm/kg.

Upon return to the laboratory, the sample was diluted to 250 mL with dispersing medium. The sample was then poured into a strainer bag, and dispersed in a Stomacher for 30 seconds at normal setting. After foaming settled down, the dispersed sample was poured into a 250 mL centrifuge tube and spun at (900×g) rpm for 10 minutes at 4° C. The supernatant was poured off and the pellet resuspended in 60 mL dispersing medium. The pellet was disrupted with a pipette tip. Thirty mL of the sample was placed in each of two 50 mL tubes. To each tube 10 mL of Histopaue (room temperature) was added from the bottom up. The tubes were centrifuged at (210×g) rpm for 30 minutes at room temperature in a table top centrifuge with the brake off. Using a transfer pipette, the top layer was discarded until about 2–3 mL above the pellet interface (smooth white band). The remaining fluid and interface is then removed (nothing lower than interface is removed). Supernatants from both tubes were combined and resuspended to 150 mL with dispersing medium. The samples were centrifuged at (900×g) rpm for 10 minutes at 4° C. and the pellet resuspended up to 10 mL in dispersing medium. The pellet was dispersed with an 18 gauge blunt needle prior to the next step. Five mL was removed from two percoll gradients with a transfer pipette, and 5 mL of the sample suspension was poured over each gradient. Percoll gradients were prepared as follows: 1 gm of sodium bicarbonate was added to 100 mL of distilled water. 9.6 gm of minimum essential medium, (MEM, Gibco BRL 41500-034) was added. Ten gm of BSA (heat shocked and fatty-acid free) (BM 100009) was mixed with 300 mL of distilled water. The BSA mixture was added to the bicarbonate/MEM solution. The solution was then added to 574 mL of percoll and filled to 1000 mL with distilled water. The resulting solution was frozen at below −20° C. for 48 hours. The percoll solution was thawed at 4° C. for 48 hours before use. The solutions were usable for 2–3 weeks.

The percoll gradients, to which 5 mL of sample suspension was added, were centrifuged at (800×g) rpm for 30 minutes at 4° C. After centrifuging, the first 5 mL were discarded. The remaining liquid above the turbid band in both tubes was saved with a transfer pipette and resuspended together to 200 mL with cold PBS. This sample is centrifuged at (900×g) rpm for 10 minutes at 4° C., the pellet was washed twice with PBS, and resuspended in dispersing medium at 1 mL/gm of original sample.

The sample was then ready for testing.

EXAMPLE 2

Preparation of Immunomagnetic Beads

Dynabeads (0.1 ml) (Dynal Dynabead M-450, 4.5 micron diameter, coated with sheep anti-mouse antibody) were vortexed and washed with 1 ml PBS by magnetically affixing beads to side of the washing tube. The beads were resuspended in 1 ml PBS for one minute and the wash step was repeated. The beads were then resuspended in 1 ml PBS and ready for use.

EXAMPLE 3

Preparation of Immunomagnetic Beads Coated with Antibody

Monoclonal capture antibody was added to the resuspended Dynabeads (see Example 2) (6 µg/25 µl Dynabeads) and incubated at 4° C. for 30 minutes on a rocker device. The beads were incubated separately with antibodies to carcinoembryonic antigen (CEA), epidermal growth factor receptor (EGFR), and antibody PCA 33.28. The Dynabeads were washed to remove any free antibody with 1 ml of PBS 4 times as described above. The beads coated with the antibody were resuspended in 1 ml PBS.

EXAMPLE 4

Immunocapture Assay with Antibody Immobilized on Dynabeads

A sample prepared as described in Example 1 was incubated with Dynabeads containing anti-CEA, anti EGFR, and PCA 33.28 prepared as described in Examples 2 and 3 at 4° C. for 20 min. on a rocker device. The sample tube was placed in a magnetic chamber on ice for 15 min. The supernatant was discarded and the beads washed three times with 1 ml of PBS in a magnetic chamber (Dynal MPC-6) on ice for three minutes each. The Dynabeads contain the colorectal epithelial cells or fragments thereof complexed with the capture antibody.

25 µL of the bead suspension was smeared on a glass microscopic slide, air dried, and stained by an immunoperoxidase method for carcinoembryonic antigen as follows. The slide was incubated with a monoclonal antibody against CEA (Biodesign International) Catalog H45655M, clone 9201) for 30 minutes at room temperature. The slide was washed and then incubated with biotin-conjugated goat anti-mouse IgG for 30 minutes at room temperature. After washing, the slide was incubated with peroxidase conjugated streptavidin for 30 minutes at room temperature. Following another washing step, the slide was incubated with hydrogen peroxide and amino ethyl carbazole for 15 minutes at room temperature. Slides were then lightly counterstained with hematoxylin and mounted with a coverslip, and examined microscopically and photographed. FIG. 1 is a photomicrograph of immunocaptured colorectal epithelial cells using the above-described technique. This confirms the epithelial lineage of the captured cells by virtue of the CEA immunostaining (red reaction product of the immunostaining procedure).

EXAMPLE 5

Immunomagnetic Isolation of Malignant Colorectal Epithelial Cells

Cultured malignant colorectal epithelial cells (WIDR, available from ATCC) were spiked into stool from a patient without gastrointestinal disease at a concentration of $1 \times 10^6$ cells/gm (approximate physiologic concentration). Spiking involves mixing 4.56 grams of stool with 500 µL of a solution of 9.6 million cells/mL WIDR cells and 10 percent formalin to a volume of 27 mL. The spiked sample was dispersed in a Stomacher for 1 minute at medium speed and allowed to settle at least 1 hour on ice. Dynabeads coated with anti-CEA, anti-EGFR, and PCA 33.28 were prepared as in Examples 2 and 3. Here 12 µg antibody/500 µL bead suspension was used. Dynabeads (450 µL total in each tube) were added to sample suspension, and incubated in a rocker device for 20 minutes at 4° C. Each sample was then diluted with 5 mL PBS. Samples were then placed in a magnetic chamber on ice for 15 minutes. Supernatants were discarded, pellets were washed 5 times with 3 mL PBS in the magnetic chamber for 3 minutes. Supernatants were discarded and the beads resuspended in 1 mL PBS. Samples were smeared onto microscopic slides and stained.

Hematoxylin and eosin staining involved: fixing in 1 percent paraformaldehyde for 10 minutes; washing with tap water for 2 minutes; exposing the hematoxylin for 2 minutes; washing with tap water for 2 minutes; smearing with eosin (on towel—5–6 drops) and letting stand for 2 minutes; 15 dips in 95 percent ethanol; 15 dips in absolute ethanol; 15 dips in xylene followed by exposure to xylene for 2 minutes; and application of a coverslip.

Slides were examined under a light microscope.

Figure 2:
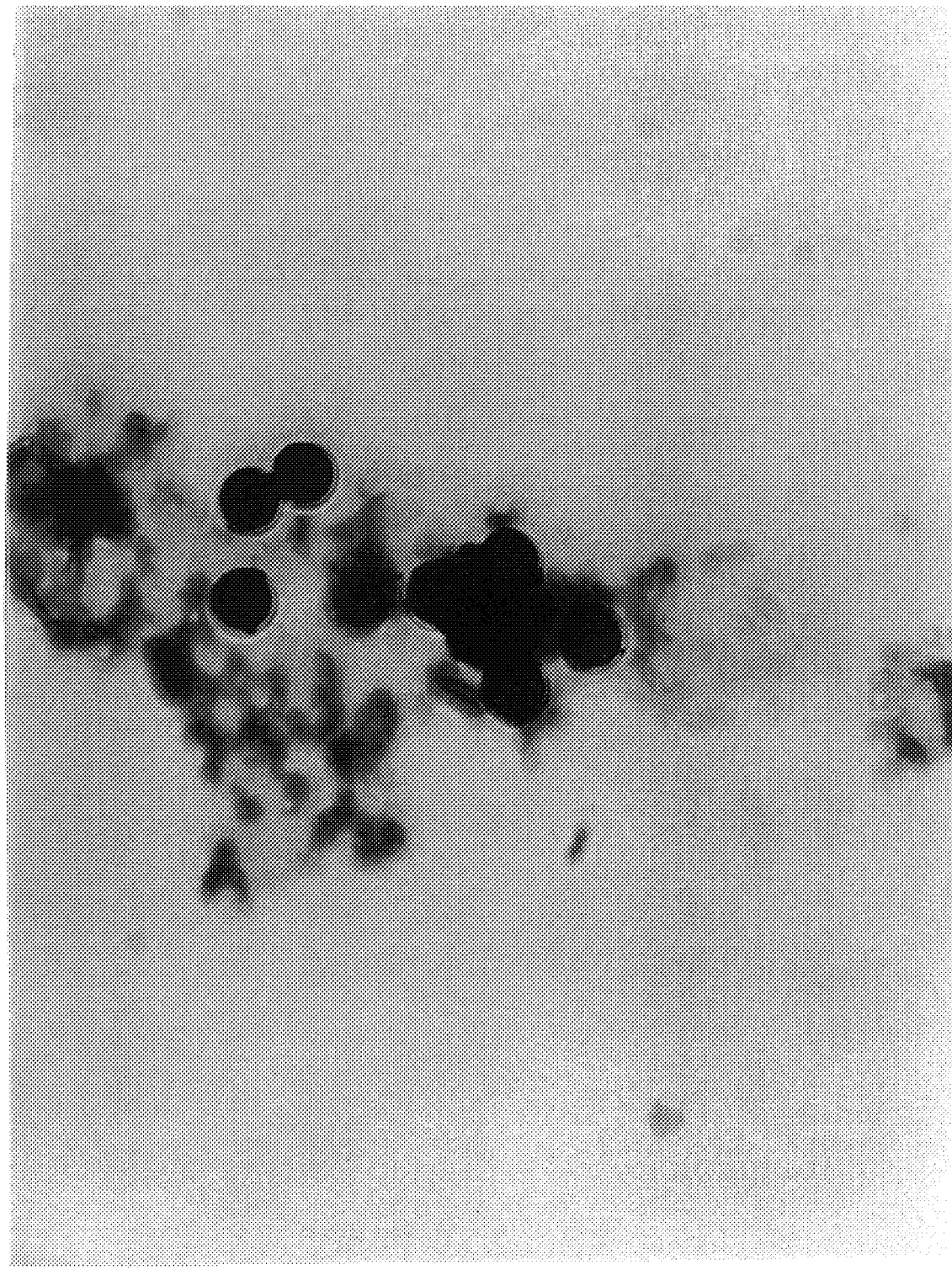
FIG. 2 is a photomicrograph of immunocaptured malignant colorectal epithelial cells from a spiked stool sample.

FIG. 2 is a photomicrograph of immunocaptured malignant colorectal epithelial cells from a spiked stool sample stained with hematoxylin and eosin as described above. By virtue of the positive stain it shows, this Figure demonstrates that the contacting of a stool sample containing malignant colorectal epithelial cells with a specific binding reagent having specificity for colorectal epithelial cells in accordance with method of the present invention is capable of capturing the malignant (or dysplastic) cells from a stool sample.

Other embodiments of the invention are within the scope of the appended claims.

What is claimed is:

1. A method of recovering colorectal epithelial cells or membrane fragments thereof from a stool sample, said method comprising the steps of:

(a) contacting a stool sample containing colorectal epithelial cells or membrane fragments thereof with an antibody or antigen binding antibody fragment having specificity for colorectal epithelial cells or membrane fragments thereof to form complexes comprising said antibody or antigen binding antibody fragment and said colorectal epithelial cells or membrane fragments thereof; and (b) separating said complexes from said sample.

2. The method of claim 1 wherein said antibody or antigen binding antibody fragment is selected from the group consisting of an antibody or antibody fragment having specificity for carcinoembryonic antigen, an antibody or antibody fragment having specificity for epidermal growth factor receptor, an antibody or antibody fragment having specificity for colon specific antigen, an antibody or antibody fragment having specificity for MUC-1 antigen, the antibody MA5 or an antigen binding fragment thereof, the antibody PCA 33.28 or an antigen binding fragment thereof, an antibody or antibody fragment having specificity for P53 antigen or mutant forms of P53 antigen, and mixtures thereof.

3. The method of claim 1 further comprising analyzing said colorectal epithelial cells or membrane fragments thereof.

4. The method of claim 3 wherein said analyzing comprises staining said colorectal epithelial cells or membrane fragments thereof and microscopically examining said colorectal epithelial cells or membrane fragments thereof.

5. The method of claim 3 wherein said analyzing comprises determining the presence or absence of dysplastic colorectal epithelial cells or membrane fragments thereof.

6. The method of claim 5 wherein determining the presence or absence of dysplastic colorectal epithelial cells or membrane fragments thereof comprises immunostaining said colorectal epithelial cells or membrane fragments thereof, said immunostaining comprises contacting said colorectal epithelial cells or membrane fragments thereof with an antibody or antigen binding antibody fragment having specificity for dysplastic colorectal epithelial cells or membrane fragments thereof.

7. A method of claim 1 wherein said antibody or antigen binding antibody fragment has specificity for dysplastic colorectal epithelial cells or membrane fragments thereof.

8. The method of claim 7 wherein said antibody or antigen binding antibody fragment is selected from the group consisting of an antibody or antibody membrane fragment having specificity for MUC-1 antigen, the antibody MA5 or an antigen binding fragment thereof, the antibody PCA 33.28 or an antigen binding fragment thereof, an antibody or antibody fragment having specificity for P53 antigen or mutant forms of P53 antigen, and mixtures thereof.

9. The method of claim 8 further comprising the step of determining the presence or absence of dysplastic colorectal epithelial cells or membrane fragments thereof in said stool sample.

10. The method of claim 9 wherein said determining comprises staining and microscopically examining said dysplastic colorectal epithelial cells or membrane fragments thereof complexed with said antibody or antigen binding antibody fragment having specificity for dysplastic colorectal epithelial cells or membrane fragments thereof.

11. The method of claim 1 wherein said contacting comprises contacting said stool sample with a magnetic bead comprising said antibody or antigen binding antibody fragment.

12. The method of claim 11 wherein said separating comprises magnetically separating said complex from said sample.

13. A method of detecting dysplastic colorectal epithelial cells or membrane fragments thereof in a stool sample, said method comprising the steps of:

(a) contacting a stool sample with a first antibody or antigen binding antibody fragment having specificity for colorectal epithelial cells or membrane fragments thereof to form first complexes comprising said first antibody or antigen binding antibody fragment and said colorectal epithelial cells or membrane fragments thereof;

(b) separating said first complexes from said sample;

(c) contacting said first complexes, or colorectal epithelial cells or membrane fragments thereof recovered from said first complexes, with a second antibody or antigen binding antibody fragment having specificity for dysplastic colorectal epithelial cells or membrane fragments thereof to form second complexes comprising said second antibody or antigen binding antibody fragment and said dysplastic colorectal epithelial cells or membrane fragments thereof;

(d) separating said second complexes; and (e) determining the presence or absence of dysplastic colorectal epithelial cells in said stool sample.

14. The method of claim 13 wherein determining the presence or absence of dysplastic colorectal epithelial cells or membrane fragments thereof comprises contacting said second complexes with a third antibody or antigen binding antibody fragment having specificity for said second antibody or antigen binding antibody fragment, separating bound third antibody or antigen binding antibody fragment from free third antibody or antigen binding antibody fragment, and determining the presence of bound third antibody or antigen binding antibody fragment.

15. An article of manufacture comprising packaging material and reagents contained within said packaging material, wherein said reagents are effective for recovering colorectal epithelial cells or membrane fragments thereof from stool, and wherein said packaging material comprises a label indicating that said reagents can be used for recovering colorectal epithelial cells or membrane fragments thereof from stool, and wherein said reagents comprise a antibody or antigen binding antibody fragment having specificity for colorectal epithelial cells or membrane fragments thereof.

\* \* \* \* \*